US00PP29819P3

(12) United States Plant Patent
Hofmann

(10) Patent No.: US PP29,819 P3
(45) Date of Patent: Nov. 6, 2018

(54) ***HELIOPSIS* PLANT NAMED 'INHELSODOR'**

(50) Latin Name: *Heliopsis helianthoides*
Varietal Denomination: Inhelsodor

(71) Applicant: Silvia Hofmann, Mainz (DE)

(72) Inventor: Silvia Hofmann, Mainz (DE)

(73) Assignee: INNOVAPLANT ZIERPFLANZEN GmbH & Co. KG, Gensingen (DE)

( * ) Notice: Subject to any disclaimer, the term of this patent is extended or adjusted under 35 U.S.C. 154(b) by 37 days.

(21) Appl. No.: 15/530,747

(22) Filed: Feb. 22, 2017

(65) Prior Publication Data

US 2018/0242504 P1 Aug. 23, 2018

(51) Int. Cl.
*A01H 5/02* (2018.01)

(52) U.S. Cl.
USPC ..... Plt./437

(58) Field of Classification Search
USPC ..... Plt./437
See application file for complete search history.

*Primary Examiner* — Keith O Neal Robinson
(74) *Attorney, Agent, or Firm* — C. A. Whealy

(57) ABSTRACT

A new and distinct cultivar of *Heliopsis* plant named 'Inhelsodor', characterized by its relatively compact and upright plant habit; freely branching habit; freely flowering habit; large single-type inflorescences with dark yellow-colored ray florets; and good garden performance.

1 Drawing Sheet

Botanical designation: *Heliopsis helianthoides.*
Cultivar denomination: 'INHELSODOR'.

BACKGROUND OF THE INVENTION

The present invention relates to a new and distinct cultivar of *Heliopsis* plant, botanically known as *Heliopsis helianthoides* and hereinafter referred to by the cultivar name 'Inhelsodor'.

The objective of the breeding program is to create new compact and freely branching *Heliopsis* plants with attractive ray and disc floret colors and good garden performance.

The new *Heliopsis* plant is the result of an open pollination of a proprietary selection of *Heliopsis helianthoides* identified as code number Hel 12 3-1, not patented, the female, or seed, parent with an unknown selection of *Heliopsis helianthoides* as the male, or pollen, parent. The new *Heliopsis* plant was discovered and selected by the Inventor as a single flowering plant from within a population of plants of the stated open pollination in a controlled greenhouse environment in Heidesheim, Germany in September, 2013.

Asexual reproduction of the new *Heliopsis* plant by divisions was first conducted in Gensingen, Germany in March, 2014. Asexual reproduction by divisions and by vegetative tip cuttings has shown that the unique features of this new *Heliopsis* plant are stable and reproduced true to type in successive generations.

SUMMARY OF THE INVENTION

Plants of the new *Heliopsis* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of the new

*Heliopsis* plant. These characteristics in combination distinguish 'Inhelsodor' as a new and distinct *Heliopsis* plant:

1. Relatively compact and upright plant habit.
2. Freely branching habit.
3. Freely flowering habit.
4. Large single-type inflorescences with dark yellow-colored ray florets.
5. Good garden performance.

Plants of the new *Heliopsis* differ from plants of the female parent selection:

1. Plants of the new *Heliopsis* are more compact and have shorter internodes than plants of the female parent selection.
2. Plants of the new *Heliopsis* are more freely branching and denser than plants of the female parent selection.

Plants of the new *Heliopsis* can be compared to plants of *Heliopsis helianthoides* 'Tuscan Sun', disclosed in U.S. Plant Pat. No. 18,763. In side-by-side comparisons, plants of the new *Heliopsis* differ primarily from plants of 'Tuscan Sun' in the following characteristics:

1. Plants of the new *Heliopsis* are more compact than plants of 'Tuscan Sun'.
2. Ray florets of plants of the new *Heliopsis* are darker yellow in color than ray florets of plants of 'Tuscan Sun'.

Plants of the new *Heliopsis* can also be compared to plants of *Heliopsis helianthoides scabra* 'Loraine Sunshine', disclosed in U.S. Plant Pat. No. 10,690. In side-by-side comparisons, plants of the new *Heliopsis* differ primarily from plants of 'Loraine Sunshine' in the following characteristics:

1. Plants of the new *Heliopsis* are more compact than plants of 'Loraine Sunshine'.
2. Plants of the new *Heliopsis* are more freely branching than plants of 'Loraine Sunshine'.
3. Plants of the new *Heliopsis* have solid green-colored leaves whereas plants of 'Loraine Sunshine' have variegated leaves.

4. Ray florets of plants of the new *Heliopsis* are darker yellow in color than ray florets of plants of 'Loraine Sunshine'.

BRIEF DESCRIPTION OF THE PHOTOGRAPHS

The accompanying photographs illustrate the overall appearance of the new *Heliopsis* showing the colors as true as it is reasonably possible to obtain in colored reproductions of this type. Colors in the photographs may differ slightly from the color values cited in the detailed botanical description which accurately describe the colors of the new *Heliopsis* plant.

The photograph at the top of the sheet comprises a side perspective view of a typical flowering plant of 'Inhelsodor' grown in a container.

The photograph at the bottom of sheet is a close-up view of a typical flowering plant of 'Inhelsodor'.

DETAILED BOTANICAL DESCRIPTION

The aforementioned photographs and following observations and measurements describe plants grown during the winter in 10-cm containers in an acrylic-covered greenhouse in Carleton, Mich. and under cultural practices typical of commercial potted *Heliopsis* production. During the production of the plants, day and night temperatures ranged from 18° C. to 30° C. Plants were 13 weeks old when the photographs and description were taken. In the following description, color references are made to The Royal Horticultural Society Colour Chart, 2007 Edition, except where general terms of ordinary dictionary significance are used.

Botanical classification: *Heliopsis helianthoides* 'Inhelsodor'.

Parentage:

*Female, or seed, parent*.—Proprietary selection of *Heliopsis helianthoides* identified as code number Hel 12 3-1, not patented.

*Male, or pollen, parent*.—Unknown selection of *Heliopsis helianthoides*, not patented.

Propagation:

*Type*.—Terminal vegetative cuttings.

*Time to initiate roots, summer*.—About seven to nine days at ambient temperatures ranging from about 18° C. to 27° C.

*Time to initiate roots, winter*.—About nine to eleven days at ambient temperatures ranging from about 18° C. to 24° C.

*Time to produce a rooted young plant, summer*.—About four to five weeks at ambient temperatures ranging from about 18° C. to 27° C.

*Time to produce a rooted young plant, winter*.—About five to seven weeks at ambient temperatures ranging from about 16° C. to 21° C.

*Root description*.—Medium in thickness, fibrous; close to white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Herbaceous perennial; relatively compact and upright plant habit; moderately vigorous growth habit and moderate growth rate.

*Branching habit*.—Freely branching growth habit with about four primary branches, each will develop about six to eight secondary lateral branches with development.

*Plant height, soil level to top of foliar plane*.—About 27 cm to 34 cm.

*Plant height, soil level to top of floral plane*.—About 35 cm to 44 cm.

*Plant width*.—About 22 cm.

*Lateral branches*.—Length: About 14 cm. Diameter: About 4 mm. Internode length: About 4.8 cm to 5 cm. Strength: Strong; young stems, flexible. Aspect: About 35° to 45° from vertical. Texture: Sparsely pubescent. Luster: Matte to slightly semi-glossy. Color: Initially, close to 146B and at the internodes, closer to 146C; with development, color becoming closer to 187A.

Leaf description:

*Arrangement*.—Opposite, simple.

*Length*.—About 8 cm.

*Width*.—About 5.6 cm.

*Shape*.—Lanceolate.

*Apex*.—Acute; reflexing with development.

*Base*.—Obtuse with truncate tendencies.

*Margin*.—Irregularly serrate.

*Texture, upper and lower surfaces*.—Scaberulose to scabrous; rugulose with prominent reticulate veining.

*Luster, upper and lower surfaces*.—Matte.

*Venation*.—Reticulate.

*Color*.—Developing leaves, upper and lower surfaces: Close to 146B. Fully expanded leaves, upper surface: Close to N137A; venation, close to 146C. Fully expanded leaves, lower surface: Close to 137B; venation, close to 146C.

*Petioles*.—Length: About 7 mm. Diameter: About 2 mm. Strength: Moderately strong. Texture, upper and lower surfaces: Scattered pubescence. Luster, upper and lower surfaces: Semi-glossy. Color, upper surface: Close to 146A. Color, lower surface: Close to 146D.

Inflorescence description:

*Inflorescence form and arrangement*.—Single-type terminal and axillary inflorescences held above and beyond the foliar plane on strong peduncles; ray and disc florets arranged acropetally on a receptacle; inflorescences face mostly upright to outwardly.

*Flowering habit*.—Freely flowering habit with about eleven to twelve inflorescence buds and open inflorescences per plant.

*Flowering season*.—Plants flower during the spring and summer in Germany; flowering continuous during this period; plants begin flowering about six weeks after transplanting rooted cuttings into containers.

*Inflorescence longevity*.—Inflorescences last about seven to ten days on the plant; inflorescences persistent.

*Fragrance*.—Present, slightly sour.

*Inflorescence buds*.—Height: About 2.2 cm. Diameter: About 2.7 cm. Shape: Rounded, flattened. Texture: Slightly rough with small hairs. Luster: Matte. Color: Close to 144A; color becoming closer to 151A with development.

*Inflorescence size*.—Diameter: Large, about 9.5 cm. Depth (height): About 3 cm. Diameter of disc: About 2.5 cm. Receptacle diameter: About 2.8 cm. Receptacle height: About 7 mm.

*Receptacle shape*.—Flattened rounded.

*Receptacle color*.—Close to 146B.

*Ray florets*.—Quantity per inflorescence and arrangement: About 30 arranged in about 2 to 2.5 whorls. Length: About 4 cm. Width: About 1.2 cm. Shape: Lanceolate. Apex: Emarginate. Base: Attenuate. Margin: Entire. Aspect: When developing, angled slightly upright; with development, becoming horizontal to curling downward. Texture, upper and lower surfaces: Smooth, glabrous; velvety; longitudinal ridges. Luster, upper and lower surfaces: Matte. Color: When opening, upper surface: Close to 153C. When opening, lower surface: Close to 151A to 151B. Fully opened, upper surface: Close to 15A; venation, close to 15A; color becoming closer to 14A with development. Fully opened, lower surface: Close to 15C; venation, close to 145B to 145C; color becoming closer to 14C with development.

*Disc florets*.—Quantity per inflorescence and arrangement: About 560 spirally arranged in about 14 to 16 whorls at the center of the receptacle. Length: About 8 mm. Diameter: About 2 mm. Shape: Tubular with five free apical lobes. Apex: Acute. Texture, inner and outer surfaces: Smooth, glabrous. Luster, inner and outer surfaces: Matte. Color, immature, inner and outer surfaces: Close to 17A. Color, mature, inner and outer surfaces: Close to 21A; towards the apex, close to 145A.

*Phyllaries*.—Quantity per inflorescence and arrangement: About 28 arranged in about three whorls. Length: About 1 cm. Width: About 6 mm. Shape: Broadly lanceolate. Apex: Acute. Base: Truncate. Margin: Entire. Texture, upper and lower surfaces: Minute pubescence. Luster, upper surface: Matte; towards the base, slightly glossy. Luster, lower surface: Matte. Color, upper surface: Close to N137B. Color, lower surface: Close to 146A.

*Peduncles*.—Length, terminal peduncle: About 11.3 cm. Diameter, terminal peduncle: About 3 mm. Length, second peduncle: About 8.7 cm. Diameter, second peduncle: About 3 mm. Angle: Terminal peduncle, erect; lateral peduncles, about 40° to 45° from vertical. Strength: Moderately strong. Texture: Pubescent. Luster: Matte. Color: Close to 146C.

*Reproductive organs*.—Androecium: Present on disc florets only; five per disc floret. Filament length: About 2.5 mm. Filament color: Close to 157C. Anther size: About 2 mm by less than 1 mm. Anther shape: Lanceolate. Anther color: Close to 200B. Pollen amount: Moderate. Pollen color: Close to 23A. Gynoecium: Present on both ray and disc florets; one per floret. Pistil length: About 9 mm. Stigma diameter: Less than 1 mm. Stigma shape: Bi-parted. Stigma color: Close to 15A. Style length: About 4 mm. Style color: Close to 15B to 15C. Ovary color: Close to 157A.

*Seeds and fruits*.—Seed and fruit production has not been observed on plants of the new *Heliopsis*.

Disease & pest resistance: Plants of the new *Heliopsis* have not been shown to be resistant to pathogens and pests common to *Heliopsis* plants.

Garden performance: Plants of the new *Heliopsis* have been observed to have good garden performance and to tolerate rain, wind and to tolerate low temperatures about 17° C.

It is claimed:

1. A new and distinct *Heliopsis* plant named 'Inhelsodor' as illustrated and described.

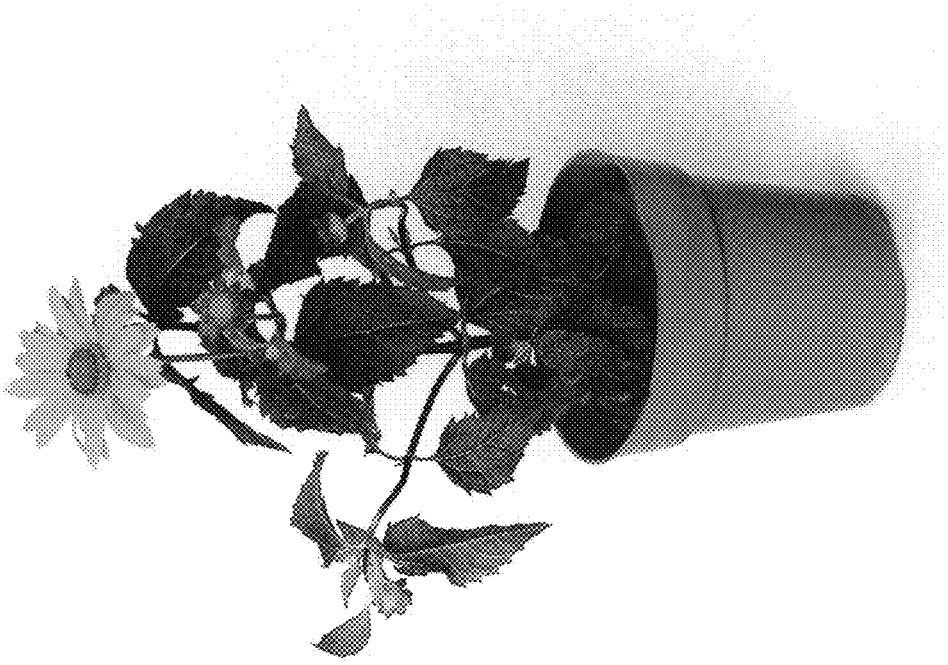
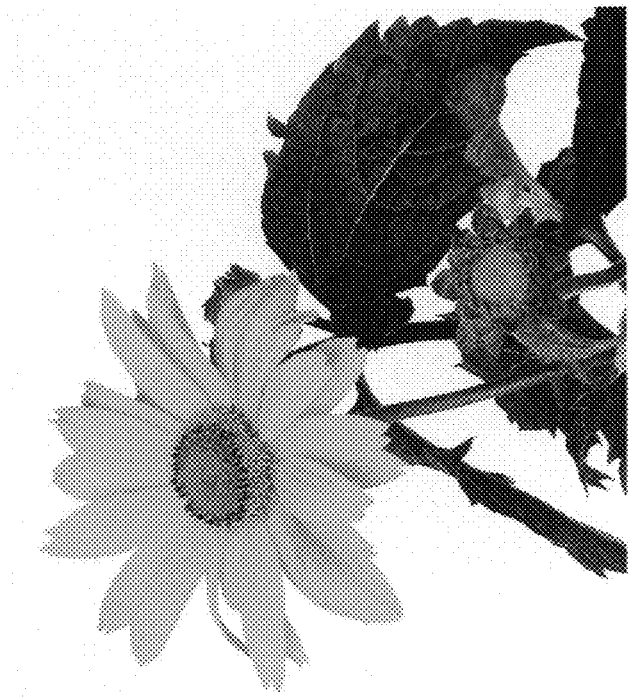

* * * * *